(12) United States Patent
Dyche et al.

(10) Patent No.: US 10,835,691 B2
(45) Date of Patent: *Nov. 17, 2020

(54) SUBSTANCE DELIVERY MODULE

(71) Applicant: KONINKLIJKE PHILIPS N.V., Eindhoven (NL)

(72) Inventors: Anthony Dyche, Hampshire (GB); Ian Thomas Petherbridge, West Sussex (GB)

(73) Assignee: Koninklijke Philips N.V., Eindhoven (NL)

( * ) Notice: Subject to any disclaimer, the term of this patent is extended or adjusted under 35 U.S.C. 154(b) by 528 days.

This patent is subject to a terminal disclaimer.

(21) Appl. No.: 14/891,466

(22) PCT Filed: Apr. 30, 2014

(86) PCT No.: PCT/EP2014/058911
§ 371 (c)(1),
(2) Date: Nov. 16, 2015

(87) PCT Pub. No.: WO2014/184006
PCT Pub. Date: Nov. 20, 2014

(65) Prior Publication Data
US 2016/0121057 A1 May 5, 2016

(30) Foreign Application Priority Data

May 17, 2013 (EP) .................................... 13168170

(51) Int. Cl.
*A61M 11/00* (2006.01)
*A61M 15/00* (2006.01)
(Continued)

(52) U.S. Cl.
CPC ......... *A61M 11/007* (2014.02); *A61M 11/005* (2013.01); *A61M 15/004* (2014.02);
(Continued)

(58) Field of Classification Search
CPC ............ A61M 11/007; A61M 15/0021; A61M 15/0036; A61M 15/0038; A61M 15/004;
(Continued)

(56) References Cited

U.S. PATENT DOCUMENTS 5,207,217 A 5/1993 Cocozza
5,337,740 A * 8/1994 Armstrong ........ A61M 15/0051
128/203.12
(Continued)

FOREIGN PATENT DOCUMENTS

DE 202012104328 U1 11/2012
EP 2062608 A2 5/2009
(Continued)

*Primary Examiner* — Quang D Thanh
*Assistant Examiner* — Jacqueline M Pinderski
(74) *Attorney, Agent, or Firm* — Daniel H. Brean

(57) ABSTRACT

A substance delivery module (4) and apparatus (2) for delivering a substance in aerosol form are disclosed. The substance delivery module (4) comprises a substance container (90), a piston (62) and an actuator (100) configured to engage the substance container (90) and urge the substance container (90) onto the piston (62), so dispensing the substance into the through passage (102) of the piston. The actuator (100) and substance container (90) are mounted in the substance delivery module (4) for relative motion, such relative motion bringing the actuator (100) into engagement with the substance container (90). The substance delivery module (4) may be assembled with an aerosol generator (10) and an aerosol delivery conduit (14) to form an apparatus (2) for delivering a substance in aerosol form. The apparatus (2) may further comprise a control module (6).

18 Claims, 22 Drawing Sheets

(51) Int. Cl.
  *B05B 1/08* (2006.01)
  *B05B 11/00* (2006.01)
  *A61M 16/00* (2006.01)

(52) U.S. Cl.
  CPC ...... *A61M 15/009* (2013.01); *A61M 15/0021* (2014.02); *A61M 15/0036* (2014.02); *A61M 15/0038* (2014.02); *A61M 15/0048* (2014.02); *A61M 15/0085* (2013.01); *B05B 1/08* (2013.01); *B05B 11/3001* (2013.01); *A61M 15/002* (2014.02); *A61M 15/0003* (2014.02); *A61M 15/0015* (2014.02); *A61M 2016/0021* (2013.01); *A61M 2016/0027* (2013.01); *A61M 2205/0205* (2013.01); *A61M 2205/0238* (2013.01); *A61M 2205/18* (2013.01); *A61M 2205/273* (2013.01); *A61M 2205/276* (2013.01); *A61M 2205/3386* (2013.01); *A61M 2205/502* (2013.01); *A61M 2205/52* (2013.01); *A61M 2205/581* (2013.01); *A61M 2205/583* (2013.01); *A61M 2205/6045* (2013.01); *A61M 2205/6054* (2013.01); *A61M 2205/8206* (2013.01)

(58) Field of Classification Search
  CPC .......... A61M 15/0048; A61M 15/0085; A61M 11/005; A61M 15/009; A61M 15/0028–0035; A61M 15/0041; A61M 15/0045–0061; B05B 1/08; B05B 11/3001
  USPC .................................................. 222/167, 168
  See application file for complete search history.

(56) References Cited

U.S. PATENT DOCUMENTS

| | | | | |
|---|---|---|---|---|
| 5,584,417 A | * | 12/1996 | Graf | A61M 15/0045 222/135 |
| 5,881,719 A | * | 3/1999 | Gottenauer | A61M 15/0045 128/203.15 |
| 6,065,472 A | | 5/2000 | Anderson | |
| 6,116,238 A | * | 9/2000 | Jackson | A61M 15/0045 128/203.12 |
| 6,186,141 B1 | * | 2/2001 | Pike | A61B 18/12 128/203.12 |
| 6,425,499 B1 | | 7/2002 | Guiffray | |
| 7,219,665 B1 | * | 5/2007 | Braithwaite | A61M 15/0045 128/203.12 |
| 8,109,267 B2 | | 2/2012 | Villax | |
| 8,113,196 B2 | | 2/2012 | Rohrschneider | |
| 8,220,455 B2 | | 7/2012 | Rohrschneider | |
| 8,235,040 B2 | | 8/2012 | Rohrschneider | |
| 8,297,277 B2 | * | 10/2012 | Rohrschneider | A61M 15/0045 128/200.14 |
| 2001/0032643 A1 | * | 10/2001 | Hochrainer | A61K 9/0078 128/200.21 |
| 2002/0170560 A1 | * | 11/2002 | Young | A61M 15/0045 128/203.15 |
| 2003/0214431 A1 | | 11/2003 | Hager | |
| 2004/0188458 A1 | * | 9/2004 | Tabata | A61M 15/0028 222/82 |
| 2006/0107957 A1 | | 5/2006 | Djupesland | |
| 2006/0157053 A1 | * | 7/2006 | Barney | A61M 15/0045 128/200.23 |
| 2007/0151562 A1 | * | 7/2007 | Jones | A61M 15/0028 128/203.21 |
| 2007/0221216 A1 | * | 9/2007 | Ganem | A61M 15/0028 128/203.12 |
| 2008/0177246 A1 | | 7/2008 | Sullivan | |
| 2008/0210229 A1 | | 9/2008 | Corbacho | |
| 2009/0223515 A1 | | 9/2009 | Watanabe | |
| 2009/0227958 A1 | * | 9/2009 | Burroughs | A61M 5/1782 604/201 |
| 2009/0236374 A1 | * | 9/2009 | Pardes | A61F 9/0008 222/494 |
| 2010/0006113 A1 | | 1/2010 | Ustsev | |
| 2010/0095957 A1 | | 4/2010 | Corbacho | |
| 2010/0126507 A1 | * | 5/2010 | Lulla | A61M 15/0045 128/203.15 |
| 2010/0258121 A1 | | 10/2010 | Kirniak | |
| 2010/0300442 A1 | * | 12/2010 | Houzego | A61M 15/0045 128/203.15 |
| 2010/0319693 A1 | | 12/2010 | Fagot | |
| 2013/0032144 A1 | | 2/2013 | Miller | |
| 2016/0089507 A1 | * | 3/2016 | Dyche | A61M 11/005 128/200.22 |

FOREIGN PATENT DOCUMENTS

| | | |
|---|---|---|
| JP | H05507671 A | 11/1993 |
| JP | 2005525578 A | 8/2005 |
| RU | 2393883 C1 | 7/2010 |
| WO | WO9200812 A1 | 1/1992 |
| WO | WO9994840 A1 | 2/1999 |
| WO | WO2012128692 A1 | 9/2012 |

\* cited by examiner

SUBSTANCE DELIVERY MODULE

TECHNICAL FIELD

The present invention relates to a substance delivery module, and particularly but not exclusively to a substance delivery module for use in an apparatus for delivering a substance in aerosol form.

BACKGROUND

Medicinal substances such as drugs and other medications are often required to be delivered in aerosol form for inhalation into the lungs of a patient. Various devices are available for delivery of medicinal substances in aerosol form, including for example nebulizers. A nebulizer is a device designed to convert a liquid substance into an aerosol which may then be inhaled by a patient, typically via a mouthpiece. Different types of nebulizer exist, using different technologies to convert the liquid substance to aerosol form. Two of the more popular technologies are jet nebulizers, which introduce compressed air to the liquid substance, and vibrating mesh nebulizers, which use a fine mesh vibrating at ultrasonic frequencies to generate a mist of substance droplets.

Medicinal substances are typically required to be delivered as controlled doses of a specific volume, and dose control is one area of nebulizer technology which has received attention. In order to provide greater control over the volume of substance delivered with each use of the nebulizer, some nebulizers have incorporated a multi dose system, in which individual doses of liquid substance are provided in place of a single liquid reservoir. An example of such a system is disclosed in US 2003/0163099, in which a plurality of sealed vials of medicinal liquid are mounted on a support member for sequential dispensing via a plunger. While such multi dose systems provide improvements in dose control over single reservoir systems, difficulties remain in assuring delivery of a maximum amount of the liquid dose to the patient. Patient operation of the apparatus can also introduce inconsistencies in the manner in which each dose of medicinal substance is dispensed.

SUMMARY

Aspects of the present invention seek to provide a module and apparatus which obviate or reduce at least one of the disadvantages mentioned above.

According to a first aspect of the present invention, there is provided a substance delivery module comprising a substance container, a piston, and an actuator, configured to engage the substance container and urge the substance container onto the piston. The actuator and substance container are mounted in the module for relative motion, such motion bringing the actuator into engagement with the substance container.

The substance container may be suitable for containing a liquid substance including for example a medicinal liquid substance such as a drug in liquid form.

The piston may comprise a passage extending therethrough.

According to some embodiments, the piston may be dimensioned to displace an internal volume of the substance container, and may thus ensure that a maximum of substance held within the container is displaced for example via a through passage of the piston. An outer diameter of the piston may sealingly engage an inner diameter of the container.

According to some embodiments, the piston may comprise a cutting element, which may be mounted on a leading surface of the piston. The cutting element may for example be operable to pierce the substance container.

According to some embodiments, the cutting element may be disposed about a leading opening of the through passage of the piston. The cutting element may define a cutting surface which is angled with respect to an axis of advance of the substance container onto the piston.

According to some embodiments, the piston may further comprise a second cutting element mounted about a rim of the leading surface of the piston.

According to some embodiments, the substance container may comprise a cup and sealing membrane and may be mounted in the module with the sealing membrane presented to a leading face of the piston.

According to some embodiments, the actuator may comprise a cam.

According to some embodiments, the module may further comprise a plurality of substance containers. According to some embodiments, one or more substance containers may contain a substance that is different to that contained in one or more other substance containers of the module. The different substances may for example be different medicinal substances.

According to further embodiments, the module may further comprise a plurality of substance containers and a plurality of pistons, each substance container being mounted for motion onto a dedicated piston.

According to some embodiments, the actuator and substance container may be mounted in the module for relative rotational motion.

According to some embodiments, the module may further comprise an annular cartridge, and the substance container may be mounted within the annular cartridge.

According to some embodiments, the module may further comprise a vent which may be located adjacent the piston and may be configured to allow gas flow away from a delivery opening of the piston.

According to some embodiments, the module may further comprise an annular cartridge lid, and the actuator may be mounted on the cartridge lid.

According to some embodiments, the cartridge and cartridge lid may be adapted for relative rotational motion about an annular axis.

According to some embodiments, the module may further comprise a coupling element, which may releasably couple the cartridge and cartridge lid for motion which may be rotational motion.

According to some embodiments, the coupling element may couple the cartridge and lid for motion in a first direction and may decouple the cartridge and lid for motion in a second direction, opposite to the first direction. Motion in the first and second directions may be rotational motion.

According to some embodiments, the coupling element may comprise an arm and cooperating toothed rack. The arm may be mounted on the cartridge and the toothed rack may be mounted on the cartridge lid.

According to another aspect of the present invention, there is provided an apparatus for delivering a substance in aerosol form, the apparatus comprising an aerosol generator, an aerosol delivery conduit in fluid communication with the aerosol generator, and a substance delivery module according to the first aspect of the present invention.

According to some embodiments, a delivery opening of the piston of the substance delivery module may be in fluid communication with the aerosol generator.

According to further embodiments, the piston of the substance delivery module may be mounted in the substance delivery module such that a delivery opening of the piston may be disposed adjacent the aerosol generator.

According to some embodiments, the apparatus may further comprise a control module, and the substance delivery module may be mounted for rotation about at least a part of the control module.

According to some embodiments, the apparatus may further comprise a biasing element, mounted between the cartridge lid and one of the aerosol delivery conduit or the control module and operable to urge the cartridge lid in the second direction.

According to some embodiments, the apparatus may further comprise a releasable locking element operable to fix a position of the cartridge relative to the control module. The releasable locking element may comprise an electromechanical lock such as a solenoid lock. The position may be a rotational position.

According to some embodiments, at least part of the apparatus may comprise an anti-microbial surface. The anti-microbial surface may be formed by coating or creating a part of the apparatus from/with an anti-microbial material (for example silver) or by treating a part of the apparatus with an antimicrobial process (for example ultra violet light).

According to another aspect of the present invention, there is provided a method of using an apparatus for delivering a substance in aerosol form according to the second aspect of the present invention. The method may comprise moving the substance container, piston and actuator in a first direction such that a leading opening of the piston is in communication with the aerosol generator, and moving the actuator relative to the piston and substance container in a second direction, opposite to the first direction, such that the actuator engages the substance container and urges the substance container onto the piston. Moving the apparatus components in the first and second direction may comprise rotating the components in first and second rotational directions.

These and other aspects of the invention will be apparent from and elucidated with reference to the embodiments described below.

BRIEF DESCRIPTION OF THE DRAWINGS

For a better understanding of the present invention, and to show more clearly how it may be carried into effect, reference will now be made, by way of example only, to the following drawings in which:

FIG. 10b is an enlarged view of a part of FIG. 10a;

FIG. 11b is an enlarged view of a part of FIG. 11a;

FIG. 12b is an enlarged view of a part of FIG. 12a;

FIG. 16b is an enlarged view of a part of FIG. 16a;

DETAILED DESCRIPTION

Embodiments of the present invention provide a substance delivery module and substance delivery apparatus that enable controlled delivery of a dose of substance contained within the apparatus or module. The apparatus and module may be used for example to deliver liquid medicinal substances in aerosol form.

Figure 1:
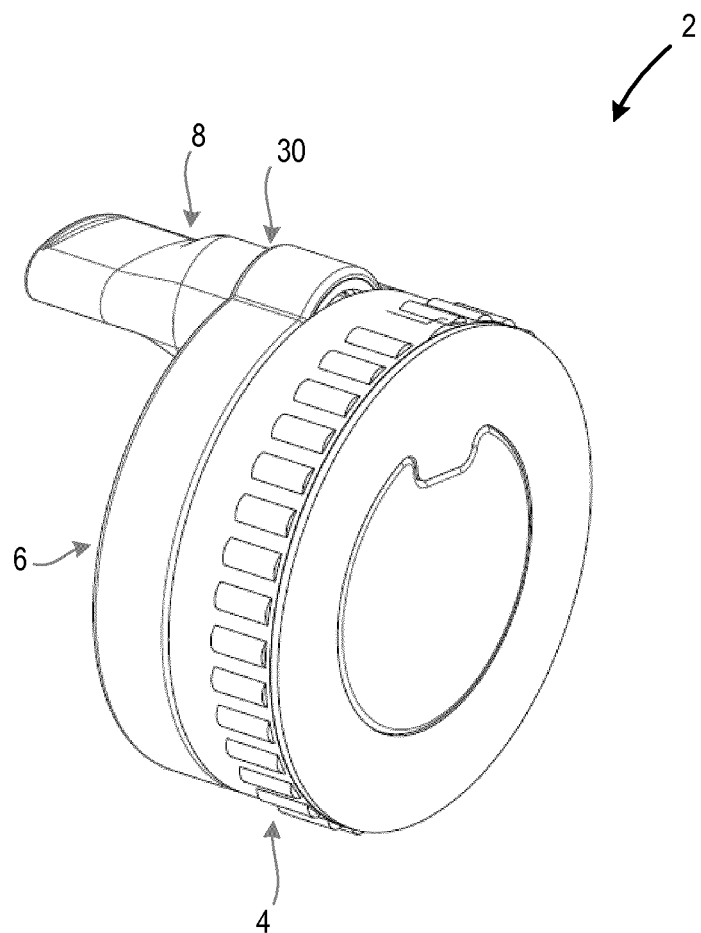
FIG. 1 is a perspective view of a nebulizer.

Referring to FIG. 1, an embodiment of an apparatus for delivering a substance in aerosol form may take the form of a nebulizer 2. The nebulizer 2 comprises a substance delivery module 4, a control module 6 and a mouthpiece 8.

Figure 2:
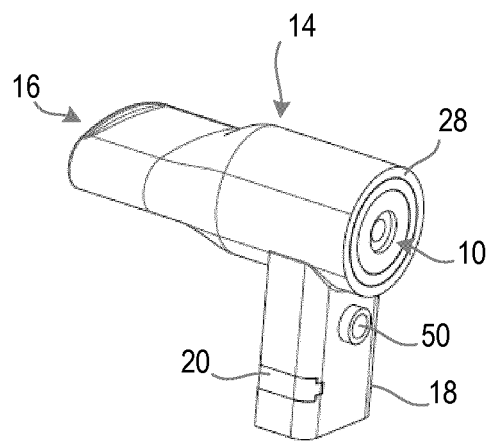
FIG. 2 is a perspective view of a mouthpiece of the nebulizer of FIG. 1.
Figure 3:
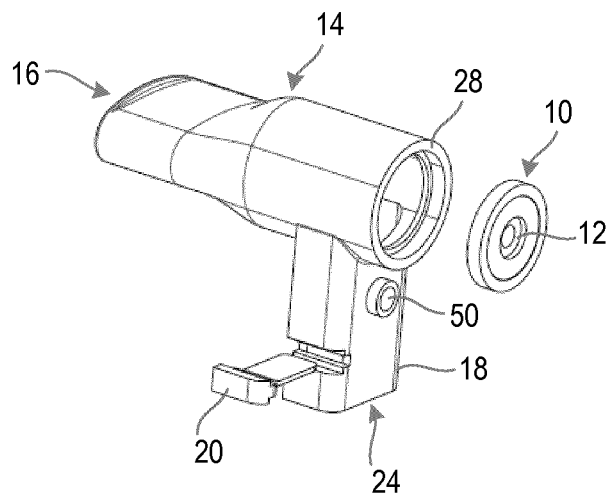
FIG. 3 is an exploded view of the mouthpiece of FIG. 2.
Figure 4:
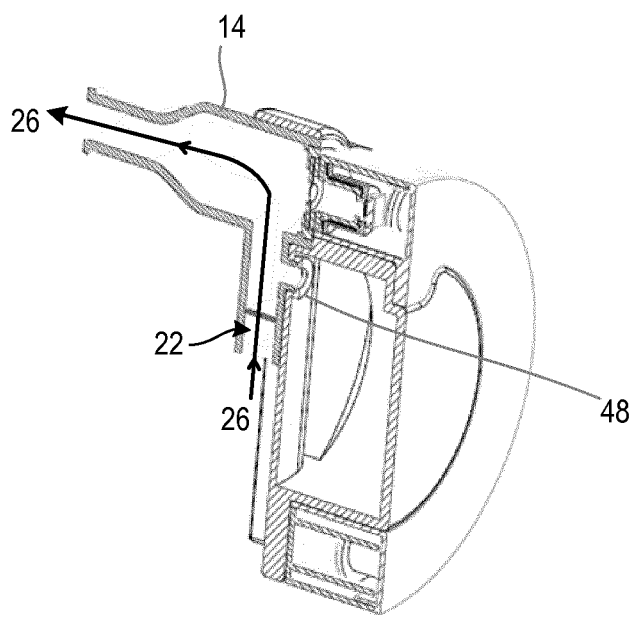
FIG. 4 is a sectioned perspective view of the nebulizer of FIG. 1.

Referring also to FIGS. 2, 3 and 4, the nebulizer further comprises an aerosol generator 10 in the form of a piezo electric mesh 12 mounted within a housing 28 in the mouthpiece 8. The mouthpiece 8 comprises an aerosol delivery conduit 14 leading from the aerosol generator 10 to an opening 16 sized to be placed in the mouth of a patient for inhalation of a substance dispensed in aerosol form by the nebulizer 2. The mouthpiece 8 further comprises an inhalation stem 18 within which is mounted a flow control valve 20. The inhalation stem comprises a through passage 22 that extends from an opening 24 via the flow control valve 20 to open into the aerosol delivery conduit 14. The inhalation stem and aerosol delivery conduit thus together define an inhalation flow path 26, as illustrated in FIG. 4. The inhalation stem further comprises an opening 50 extending through a wall of the stem to communicate with the inhalation flow path 26.

The housing 28 of the mouthpiece 8 is received within a recess 30 formed in the control module 6, such that the aerosol generator 10 is presented to, and in fluid communication with, the output of a substance feed system formed by the substance delivery module 4, as explained in further detail below.

Figure 5:
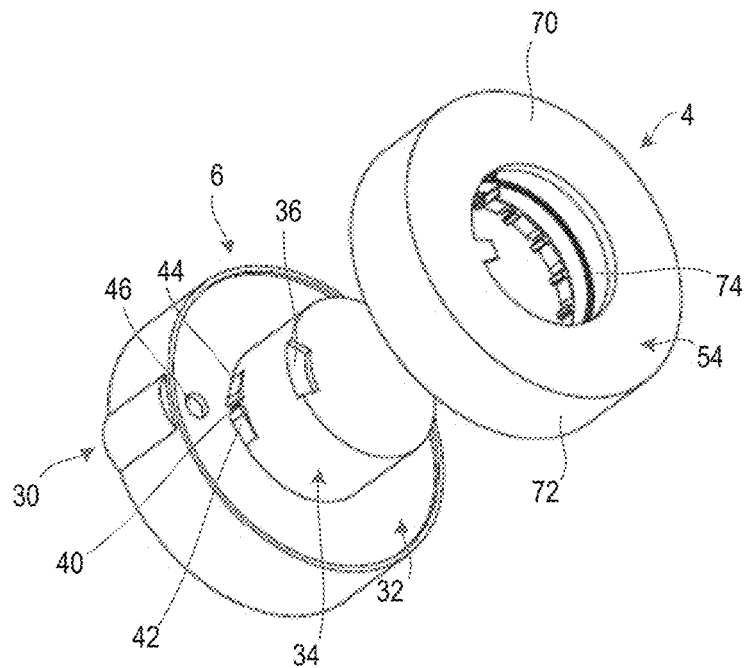
FIG. 5 is an exploded view of a substance delivery module and control module.
Figure 6:
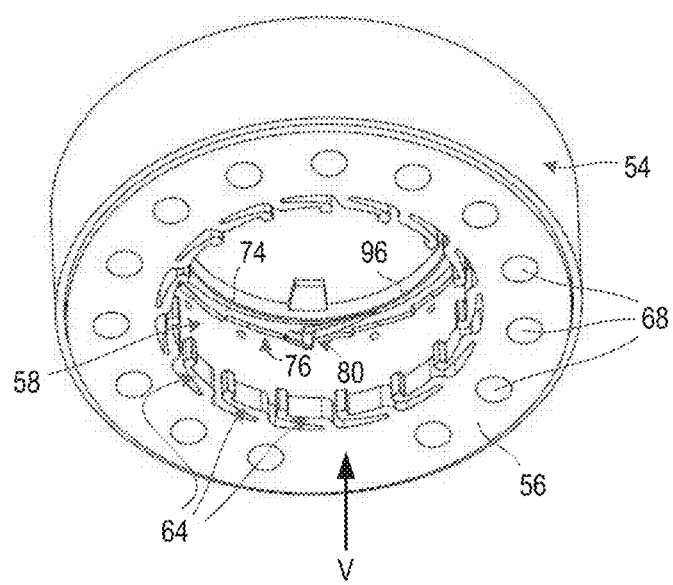
FIG. 6 is a perspective view of a substance delivery module.

Referring now to FIG. 5, the control module 6 comprises a substantially sealed unit within which is housed power and control circuitry. The power and control circuitry may include a battery or other power source, an electromechanical lock, as discussed in further detail below, an electronic tagging device such as an RFID tag, a memory and circuitry to power a patient display panel such as a screen, LED indicator light etc. The control module also houses the drive circuitry for the aerosol generator 10. The electrical connection between the aerosol generator 10 and the control module 6 may use physical contacts or inductive coupling. The functioning of the control module is discussed in detail below with respect to the operation of the nebulizer 2.

The control module 6 comprises a substantially cylindrical main body 32 and a hub 34, protruding from a planar face of the main body 32. The hub is also substantially cylindrical and includes a guide recess 36 formed on an outer planar face, which recess is dimensioned to cooperate with a guide lip 38 formed on a cartridge lid 54 of the substance delivery module 4, as discussed below. The hub 34 also comprises guide shoulders 42, 44 defining an opening 40 through which the electromechanical lock housed within the control module 6 engages with a cartridge 52 of the substance delivery module 4. As discussed above, a recess 30 is formed in the main body 32 of the control module, extending from the face opposite to that from which the hub 34 protrudes. The recess 30 is dimensioned to accept the housing 28 of the mouthpiece 8. The recess 30 communicates with a delivery passage 46 which extends through the main body 32 of the control module to open onto the face from which the hub 34 extends. The delivery passage 46 is radially aligned with the opening 40 for the electromechanical lock.

The control module 6 may also comprise an opening 48 through which a pressure sensor (not shown) may protrude. When assembled with the mouthpiece 8, the opening 48 communicates with the opening 50 on the mouthpiece 8 to allow a pressure sensor mounted within the control unit 6 to protrude into the inhalation flow path 26. The cooperating openings can be seen in the assembled sectional view of FIG. 4.

Referring now to FIGS. 5, 6, 7 and 11, the substance delivery module 4 comprises a cartridge 52 and a cartridge lid 54. The cartridge 52 comprises an annular structure having a base plate 56, inner annular wall 58, and outer annular wall 60. Mounted within the cartridge 52 is a plurality of delivery pistons 62, which will be described in further detail below. In an alternative embodiment (not shown), only a single piston 62 may be mounted in the cartridge 52. In the illustrated embodiment the pistons 62 are integrally formed with the cartridge but in alternative embodiments, the pistons may be separately formed and fixed in place in the cartridge 52. Protruding from the inner annular wall of the cartridge 52 is a plurality of indexing arms 64, substantially evenly distributed around the inner circumference of the wall 58. Each arm 64 terminates in a locking rib 66. Each of the locking ribs 66 is dimensioned to be received in the opening 40 formed between shoulders 42, 44 on the hub 34 of the control module 6. The indexing arms are resilient, able to support mild deflection such that the locking rib on the end of each arm may be disengaged from the opening 40. As illustrated most clearly in FIG. 6, the base plate 56 of the cartridge 52 comprises a plurality of openings 68, each of which corresponds to a through passage formed through a delivery piston 62 as described below.

Referring again to FIGS. 5 and 6, the cartridge lid 54 comprises a top plate 70, an outer annular wall 72 and an inner annular wall 74 that terminates in a toothed rack 76. The lid 54 is received over the cartridge 52, such that the outer annular wall 72 of the lid 54 sits radially outwardly of the outer wall 60 of the cartridge 52 and the inner wall 74 of the lid 54 sits radially inwardly of the inner wall 58 of the cartridge 52. As mentioned above, a guide lip 38 protrudes radially inwardly from the top plate 70 of the cartridge lid, and is received in the guide recess 36 on the control module 6 when the components of the nebulizer 2 are assembled. A cam 100 is mounted on an inner surface of the top plate 70, protruding towards the cartridge 52. The function of the cam is discussed below with reference to FIGS. 17 to 19.

Figure 7:
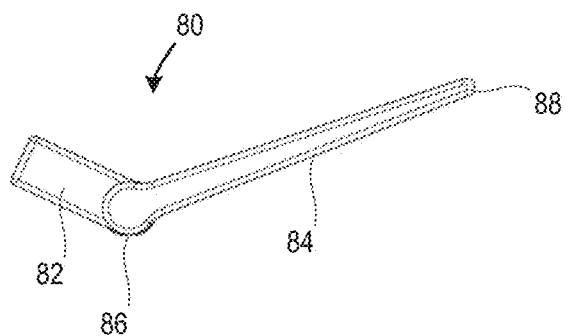
FIG. 7 is a side view of a rocker.

The lid 54 is received over the cartridge 52 with a margin allowing for relative rotational movement about the annular axis between the cartridge 52 and lid 54. Relative rotation between the cartridge 52 and lid 54 is restricted by a coupling element 80 in the form of a rocker as illustrated in FIG. 7. The rocker 80 comprises a pawl 82 and a biasing arm 84 joined at a sprung pivot point 86. The rocker 80 is mounted on the inner wall 58 of the cartridge 52 such that a free end 88 of the biasing arm 84 engages on a rim 96 formed on the inner wall 74 of the lid 54. The sprung hinge 86 acts to close the pawl towards the biasing arm 84 and in so doing forces the pawl 82 into engagement with the toothed rack 76 on the inner annular wall 74 of the lid 54. The rocker 80 thus couples the cartridge 52 to the lid 54 for movement in a first direction (clockwise rotation of the lid when viewed from above) as the pawl 82 engages on a forward face of a tooth of the toothed rack. Rotation of the lid 54 in a second direction opposite to the first direction (anticlockwise) decouples the lid 54 and cartridge 52, allowing the lid 54 to rotate relative to the cartridge 52 as the pawl 82 rides up the back face of the tooth and then falls into engagement with the next tooth.

Figure 8A:
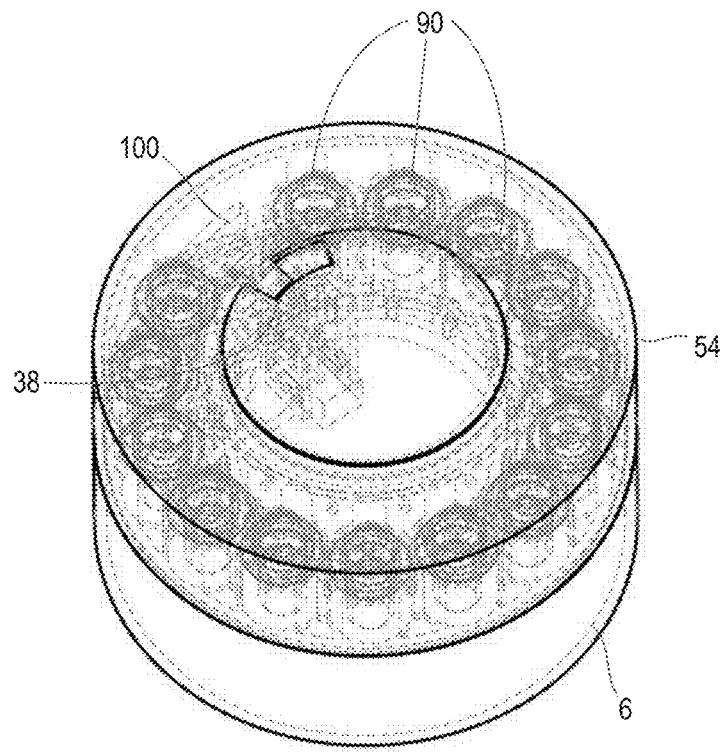
FIG. 8a is a perspective, partially transparent view of a substance delivery module mounted on a control module.
Figure 8B:
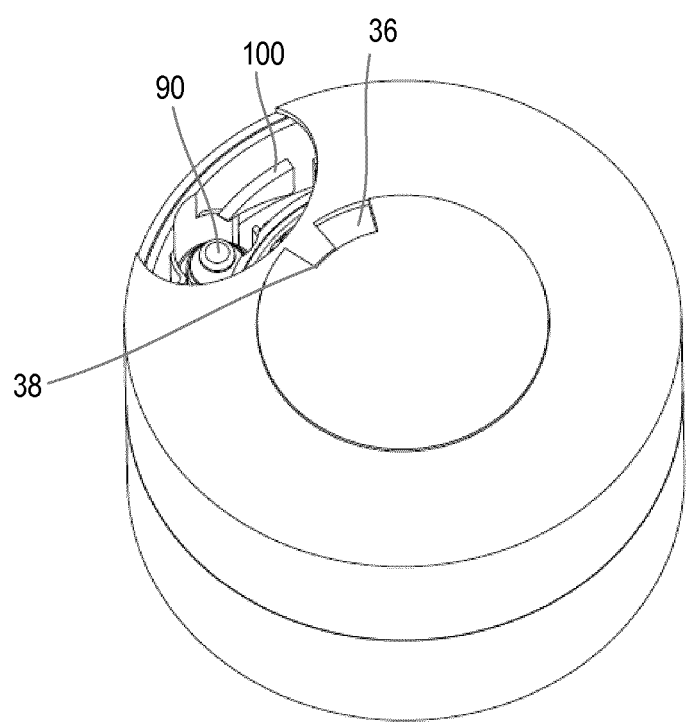
FIG. 8b is a perspective view of the modules of FIG. 8a showing a cut out view.

As discussed above, a plurality of pistons 62 are mounted within the cartridge 54. Axially aligned with each piston 62 is a substance container or vial 90. The vials can be seen in dashed outline in FIG. 8a, through the lid 54 and through the cut-out view in FIG. 8b. In the illustrated embodiment the cartridge 52 is loaded with 14 pistons and 14 vials, representing for example a one week course of drugs comprising a twice daily dose. A fifteenth position on the cartridge is vacant, to allow for the cam 100, as discussed in further detail below.

Figure 9A:
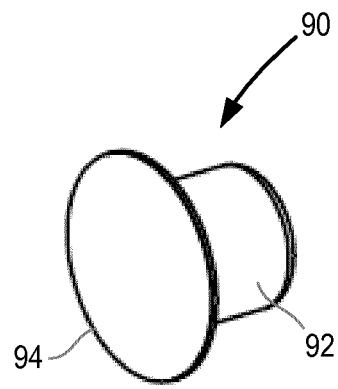
FIG. 9a is a perspective view of a substance container.
Figure 9B:
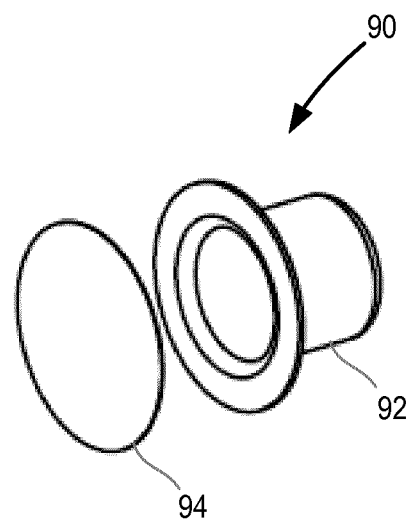
FIG. 9b is an exploded view of a substance container.
Figure 12A:
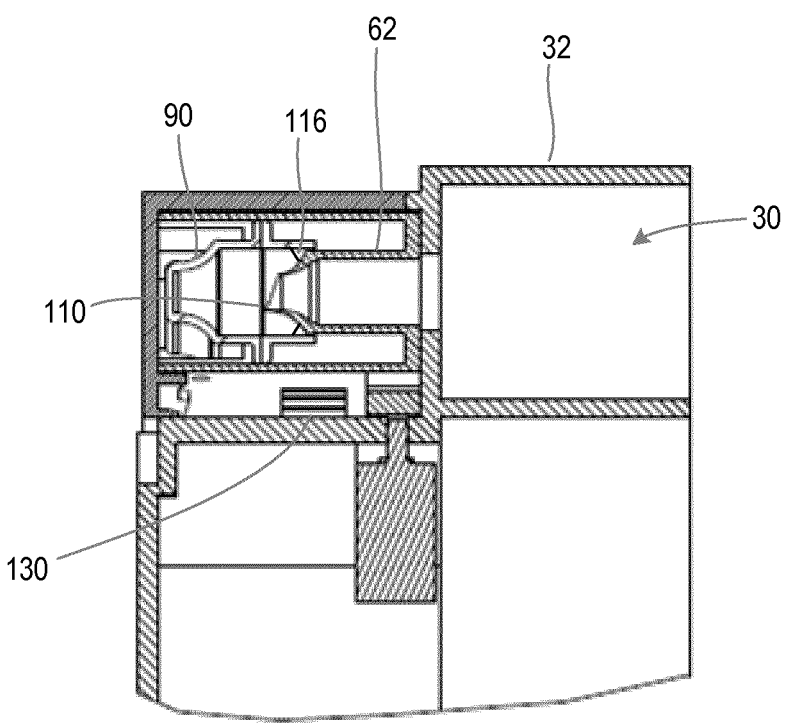
FIG. 12a is a partial sectional view of another substance delivery module and control module.
Figure 12B:
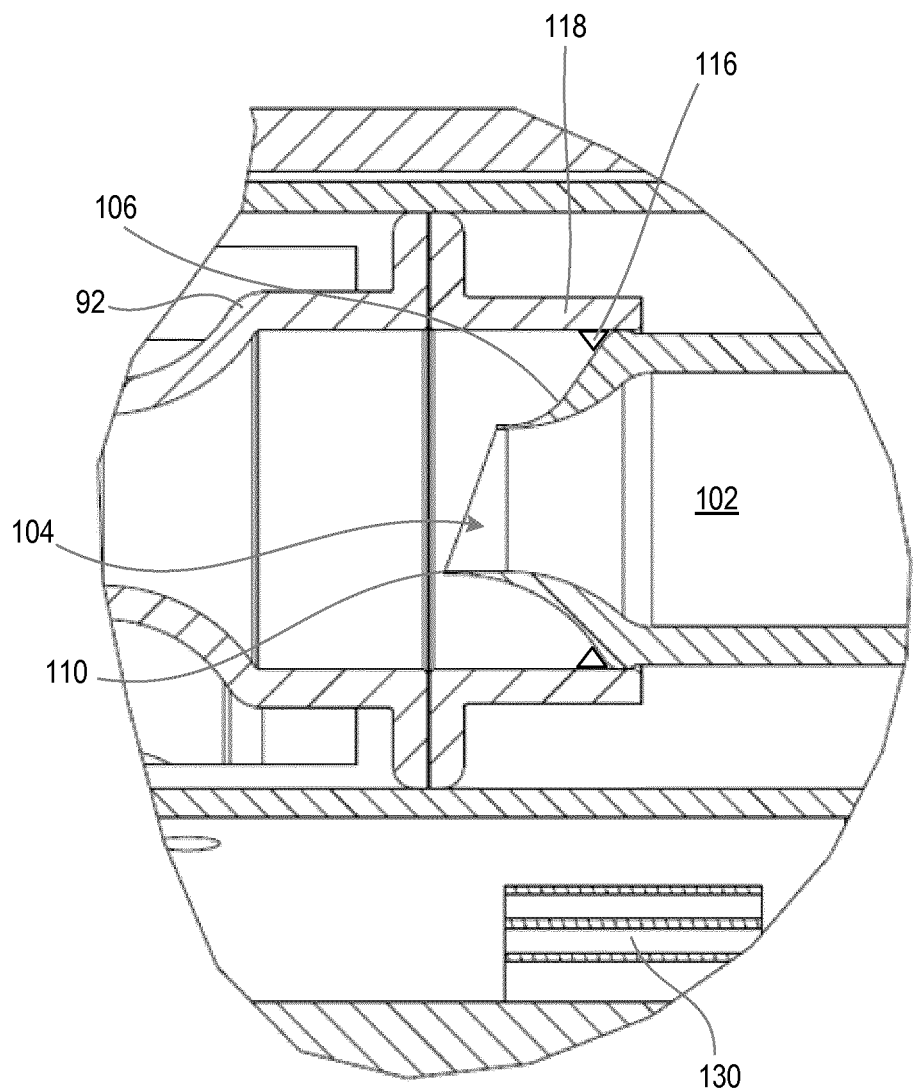

Referring now to FIG. 9, each vial 90 comprises a cup 92 and a sealing membrane 94. The substance to be dispensed is sealed within the cup by the membrane. Each vial 90 is mounted in the cartridge axially aligned with a piston 62, with the membrane 94 presented to the leading face of the piston 62. The arrangement of a piston 62 and vial 90 can be seen in detail in FIGS. 10a and 10b. The piston 62 comprises a through passage 102 extending from a leading opening 104 on a leading face 106 of the piston 62 to a delivery opening 108 which is coincident with the corresponding opening 68 formed in the base plate 56 of the cartridge 52. The leading opening 104 is surrounded by a first cutting element 110 which extends towards the membrane 94 of the vial 90 and defines an angled cutting plane 112. A sealing sleeve 118 may surround the first cutting element 110 providing sliding sealing engagement between the vial 90 and an outer surface 114 of the piston 62. The sealing sleeve 118 may also act to guide the vial 90 onto the piston 62, as discussed below. In some embodiments, the sealing sleeve 118 may be formed integrally with the vial 90. In the embodiment illustrated in FIGS. 10a and 10b, the piston 62 comprises only a single cutting element 110. However in an alternative embodiment illustrated in FIGS. 11 and 12, the piston 62 further comprises a second cutting element 116. The second cutting element also extends towards the membrane 94 of the vial 90 and is mounted about a rim of the leading surface 106 of the piston 62.

In use, the substance control module 4 is first assembled with the required drug or drugs sealed in the vials 90 and the vials 90 loaded in position adjacent their corresponding pistons 62. As mentioned above, in the illustrated embodiment the substance delivery module comprises 14 pistons and 14 vials, corresponding to a one week supply of a twice daily dose of medicinal substance. Other embodiments may comprise more or less pistons 62 as required. Alternatively, not all pistons may have a corresponding vial loaded. The cartridge 52 includes a vacant position V, in which no piston is provided. This can be seen in FIG. 6 as the position corresponding to an absent opening 68 on the base plate 56 of the cartridge 52. Once the sealed vials 90 are in position on the cartridge, the cartridge lid 54 is placed over the cartridge 52, closing the substance delivery module 4. The cartridge lid 54 is oriented such that the cam 100 protruding from an inner surface of the top plate 70 of the lid 54 occupies the vacant space V in the cartridge where no piston or vial is mounted. This initial alignment can be seen for example in FIG. 8a, in which the cam 100 is illustrated in dashed outline in the vacant position of the cartridge, and in FIG. 8b.

As the lid 54 is lowered onto the cartridge 52, the free end 88 of the rocker biasing arm 84 engages on the rim 96 of the lid 52, so urging the pawl 82 into engagement with a tooth of the toothed rack 76. A closure mechanism in the form of cooperating closing elements may ensure that the lid 54 remains in position over the cartridge 52 once the substance delivery module 4 is assembled.

The assembled substance delivery module 4 may be supplied to a patient on a weekly or other regular basis, each module 4 charged with a specific course of drug treatment. The patient may then assemble the nebulizer 2 for use as required.

Figure 13:
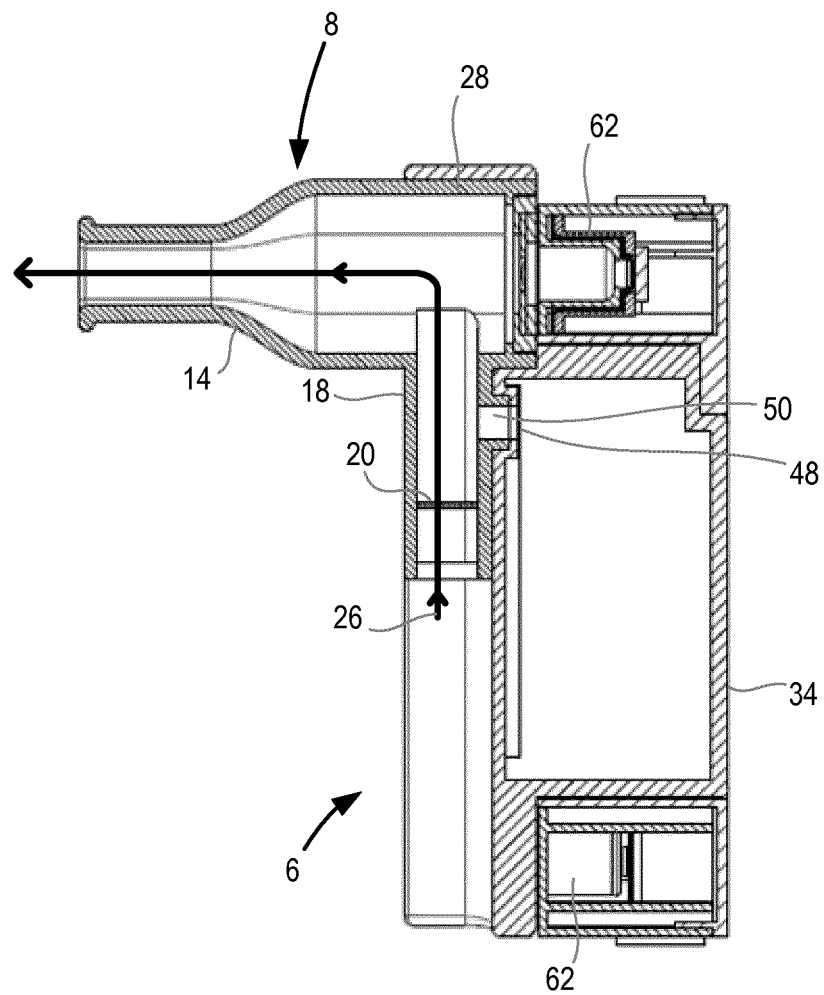
FIG. 13 is a sectional view of the nebulizer of FIG. 1.

As discussed above and illustrated in FIGS. 4 and 13, the mouthpiece 8 is mounted on the control module 6 with the housing 28 received in the recess 30 and the openings 48, 50 aligned. This presents the aerosol generator 10 to the delivery passage 46 of the control module 6. The mouthpiece 8 may be removed and reassembled with the control module 6 by the patient to allow for cleaning or replacement of the mouthpiece 8. The assembled substance delivery module 4 may then be mounted on the hub 34 of the control module 6.

Figure 14:
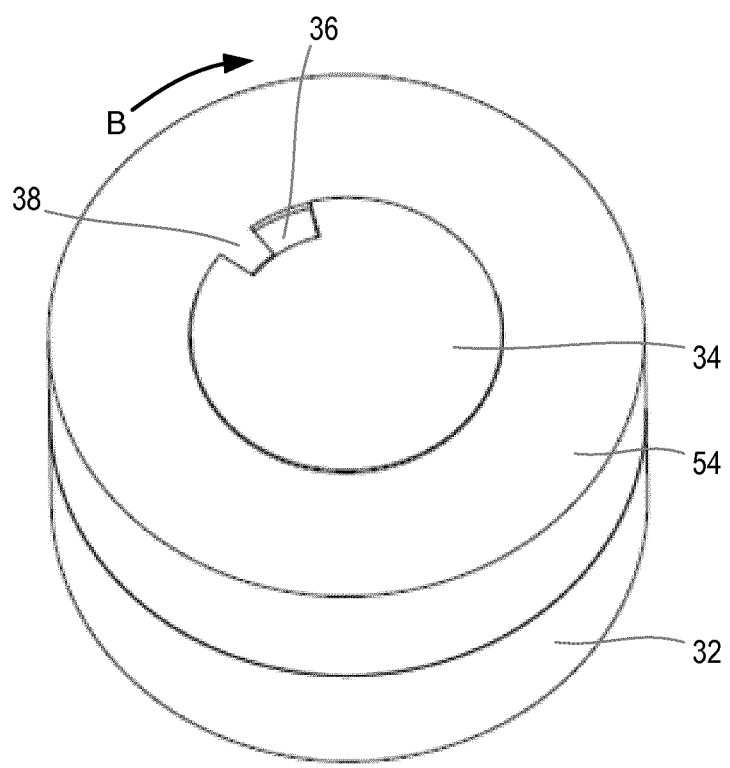
FIG. 14 is a perspective view of a substance delivery module and control module in a first position.

The guide lip 38 on the cartridge lid 54 and guide recess 36 on the control unit hub 34 cooperate to guide the patient in correctly assembling the substance delivery module 4 onto the control module 6. FIG. 14 illustrates the initial position of the guide lip 38 within the guide recess 36, aligned with the left edge of the guide recess, as viewed in the Figures (this position can also be seen in FIGS. 8a and 8b). The substance delivery module 4 slides axially onto the hub 34, at the same time engaging the indexing system formed by the electromechanical lock and indexing arms 64 of the cartridge 52.

Figure 16A:
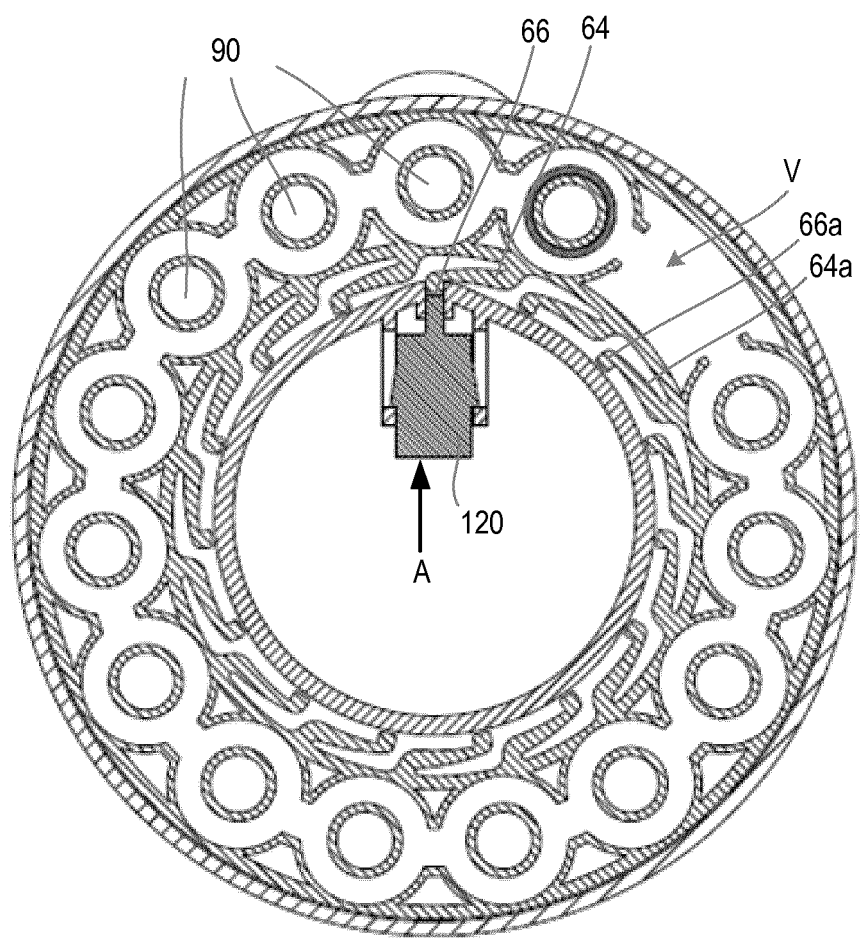
FIG. 16a is a sectional view of a substance delivery module and control module.
Figure 16B:
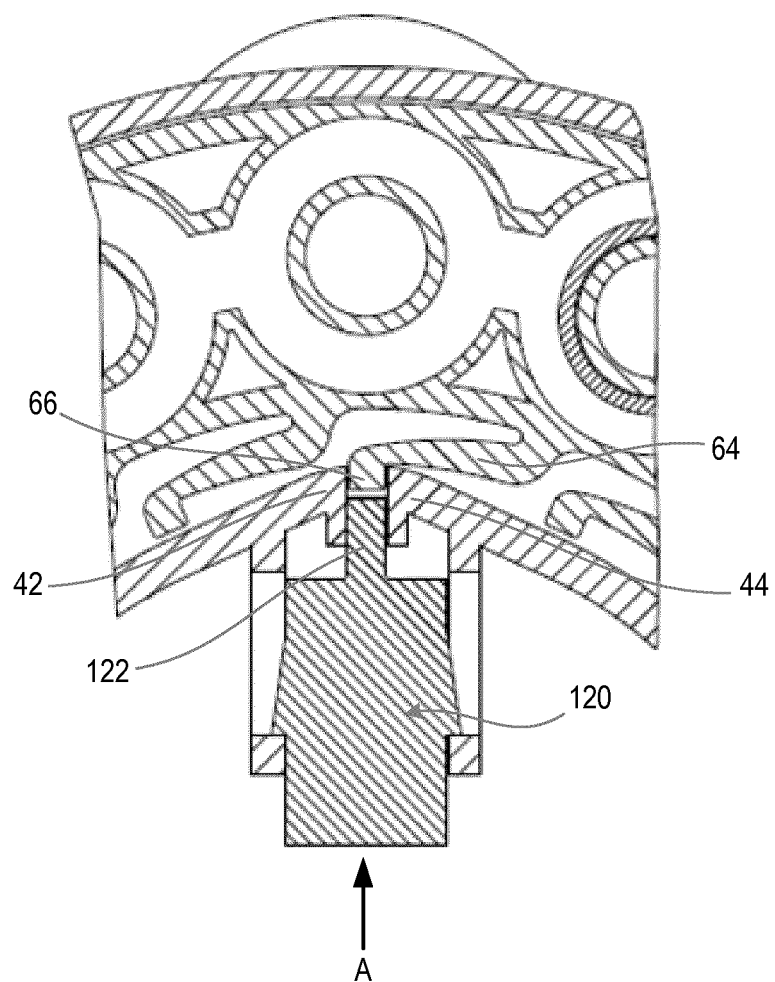

FIGS. 16a and 16b are sectional views illustrating the indexing system of the nebulizer 2, with the substance delivery module indexed two places from its initial position. With the lid 54 placed over the cartridge 52 such that the cam 100 occupies the vacant position of the cartridge 52, the guide lip 38 of the lid 54 cooperates with the guide recess 36 to ensure that the vacant position V with the cam over the top is presented to the delivery passage 46 of the control module 6, and the indexing arm 64a corresponding to the vacant position V is engaged between the shoulders 42, 44 on the hub 34. The locking rib 66a of the vacant position indexing arm 64a occupies the opening 40. The electromechanical lock mounted within the control module 6 is illustrated as solenoid lock 120 in FIGS. 18 and 19. The solenoid lock 120 comprises a locking pin 122 which occupies an inner region of the opening 40. When the solenoid lock is activated, the locking pin 106 advances into the opening in the direction indicated by arrow A. This motion disengages the locking rib 66 from the opening, allowing rotation of the cartridge 52 to the next indexing position. In the arrangement illustrated in FIGS. 16a and 16b, this indexing process has been conducted twice, indexing the cartridge two places clockwise from its initial position.

With the mouthpiece 8 and substance delivery module 4 mounted on the hub 34 of the control module 6, the nebulizer 2 is assembled and ready for first use. When a patient is ready to administer a dose of the substance contained in the nebulizer 2, the patient first powers on the nebulizer using a power button located on the control module 6. Powering on the nebulizer 2 has the effect of engaging the solenoid lock 120, such that the locking pin 122 advances into the opening 40, engaging the locking rib 66 and pushing it out of the opening 40, so allowing rotation of the cartridge 52. With the indexing system released, the patient then grasps the cartridge lid 54 and rotates the lid in a clockwise direction, as illustrated by arrow B on FIG. 14.

Figure 10A:
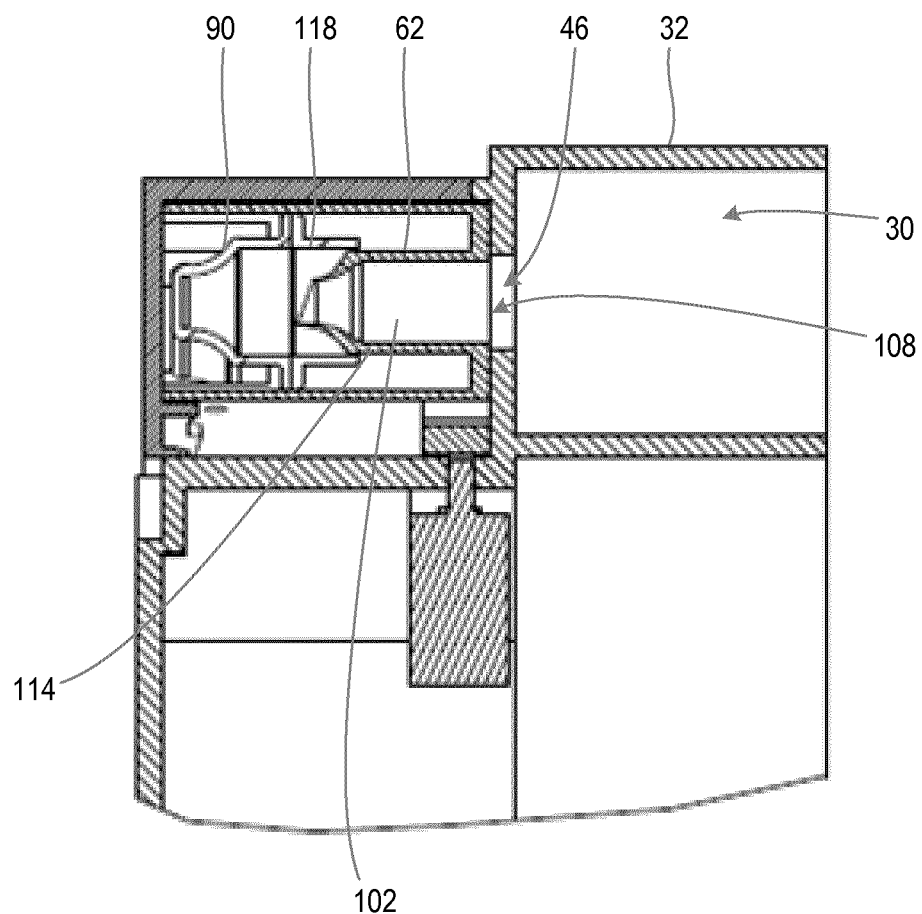
FIG. 10a is partial sectional view of a substance delivery module and control module.
Figure 10B:
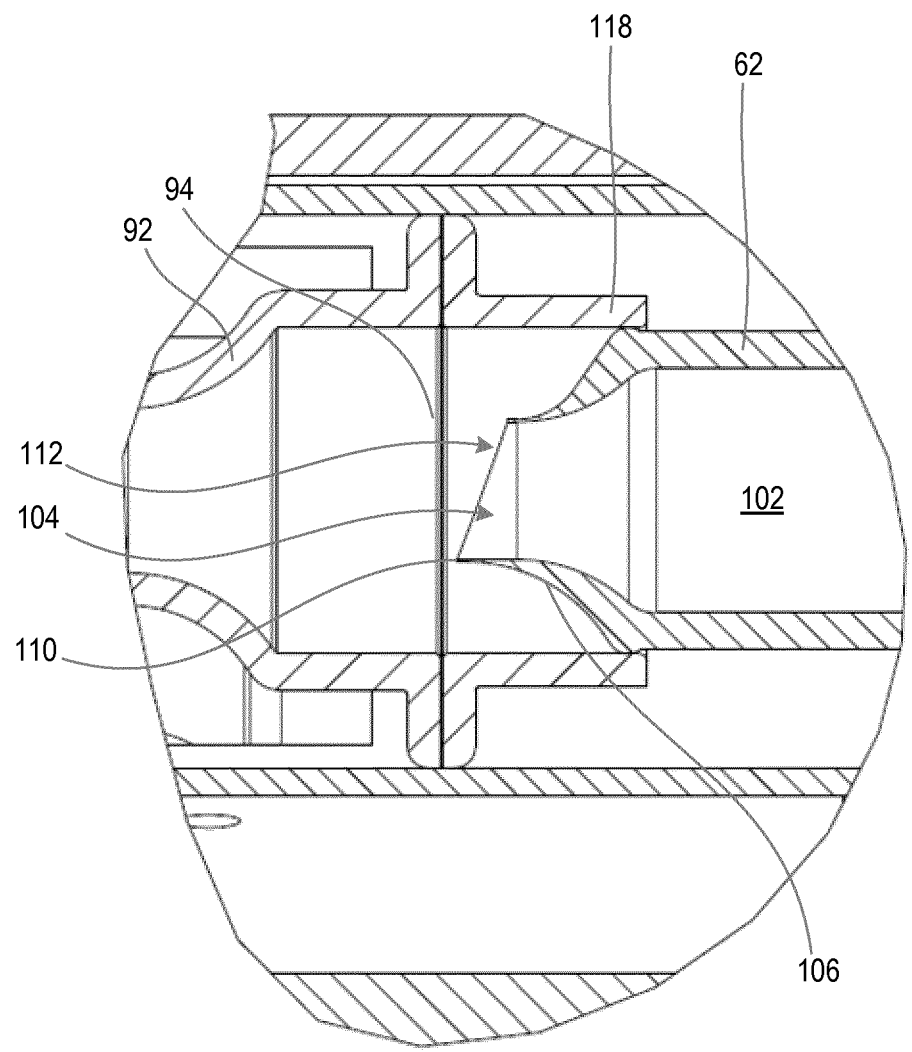
Figure 11A:
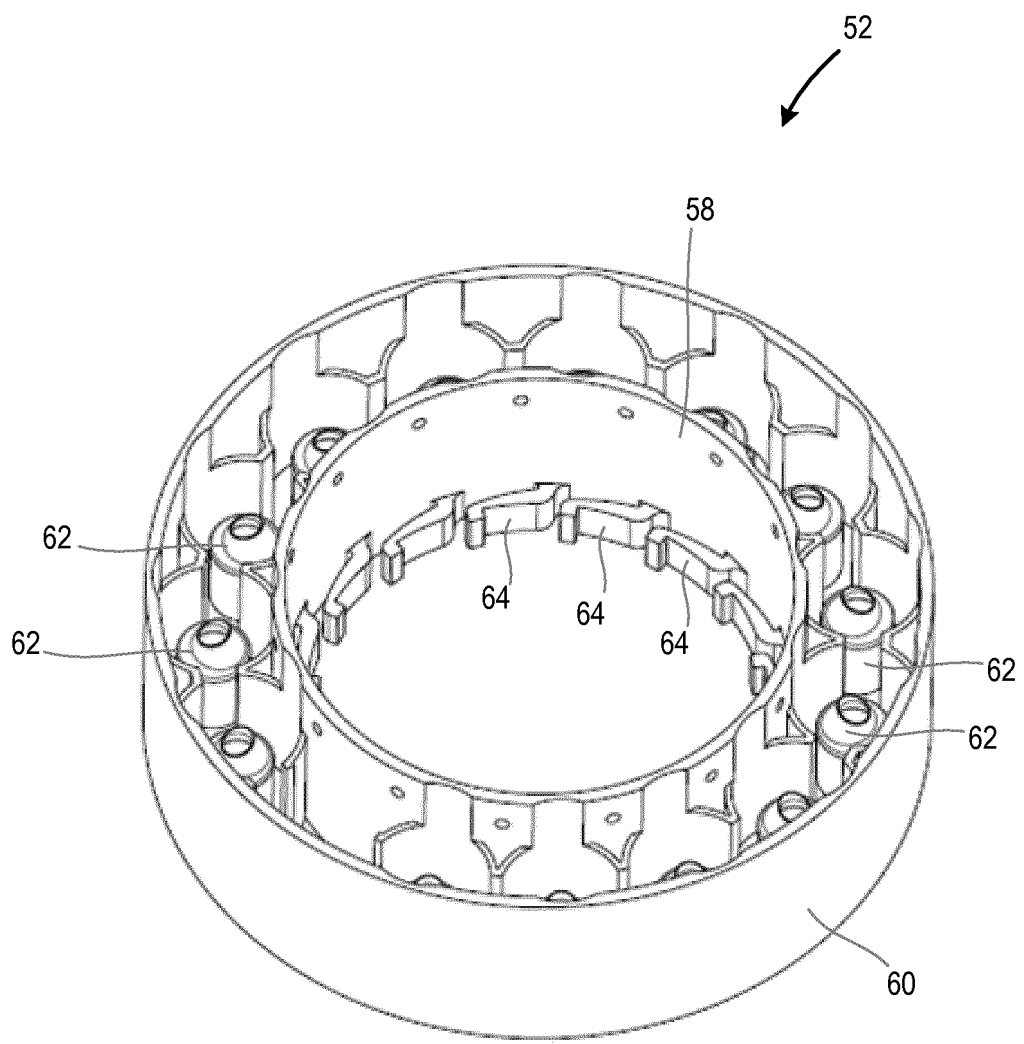
FIG. 11a is a perspective view of a cartridge.
Figure 11B:
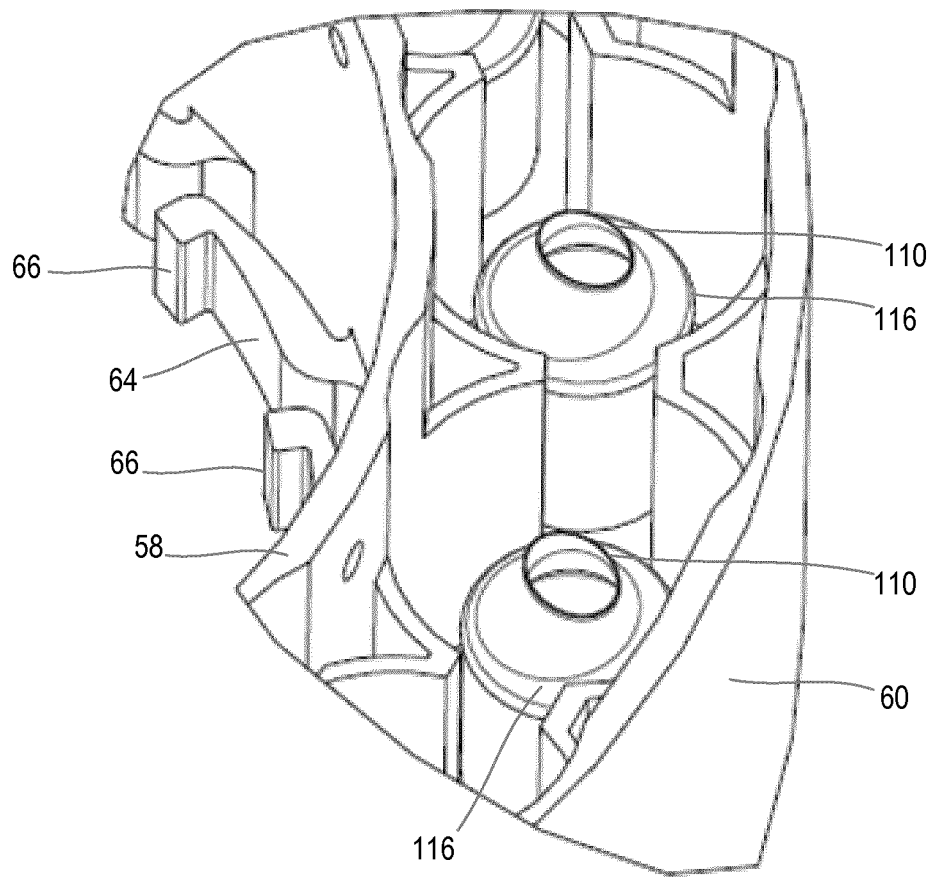
Figure 15:
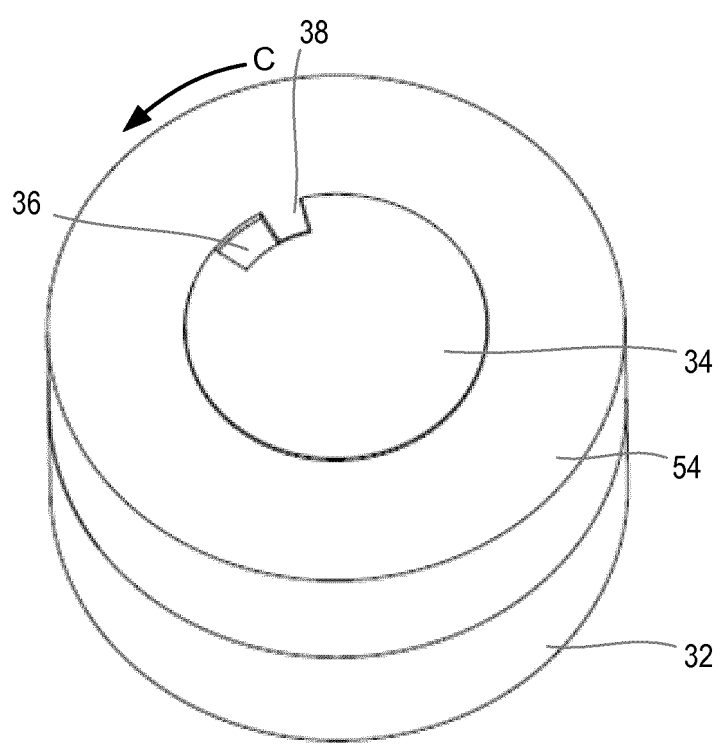
FIG. 15 is a perspective view of the substance delivery module and control module of FIG. 14 in a second position.

During the clockwise rotation of the cartridge lid 54, the rocker 80 couples the cartridge 52 and lid 54 together, as described above, causing the cartridge 52 also to rotate in a clockwise direction, until the guide lip 38 engages the right hand edge of the guide recess 36 and the locking rib 66 of the next indexing arm 64 engages in the opening 40 (position illustrated in FIG. 15). The cartridge 52 is thus indexed round by one position. Indexing of the cartridge 52 brings the first position piston 62 and vial 90 into alignment with the delivery passage 46 in the control module and the aerosol generator 10, as illustrated in FIG. 10a. The first position piston 62 and vial 90 are thus in a dispensing position and ready for dispending the dose contained in the vial 90. With the piston and vial in the dispensing position, the cartridge lid 54 is then rotated back anti clockwise to return to its original position with reference to the control module 6 (illustrated by arrow C in FIG. 15). This anticlockwise rotation may be performed by the patient or may for example be executed by a return spring. A return spring in the form of a clock spring may be incorporated into the cartridge lid or control module, such that the clock spring acts between the cartridge lid and the control module to urge the cartridge lid to rotate in an anti clockwise rotation. An example of such a spring is illustrated at 130 in FIGS. 12a and 12b. Engagement between the clock spring, the control module and the cartridge lid may be established as the substance delivery module 4 is mounted onto the control module 6.

During anticlockwise rotation of the cartridge lid 54, the lid 54 is decoupled from the cartridge 52, which is held in position by the locking rib 66 and indexing arm 64. The solenoid lock 122 that released the previous arm is returned to its disengaged position to allow engagement of the new locking rib into the opening 40. During the anticlockwise rotation of the lid 54, the pawl 82 of the rocker 80 rides up the back face of a tooth on the toothed rack before falling into engagement with the net tooth. The anticlockwise rotation of the lid 54 relative to the cartridge 52 brings the cam 100 into axial alignment with the piston 62 and vial 90 in the dispensing position. The cam 100 thus engages the vial 90, forcing it onto the piston 62.

Figure 17:
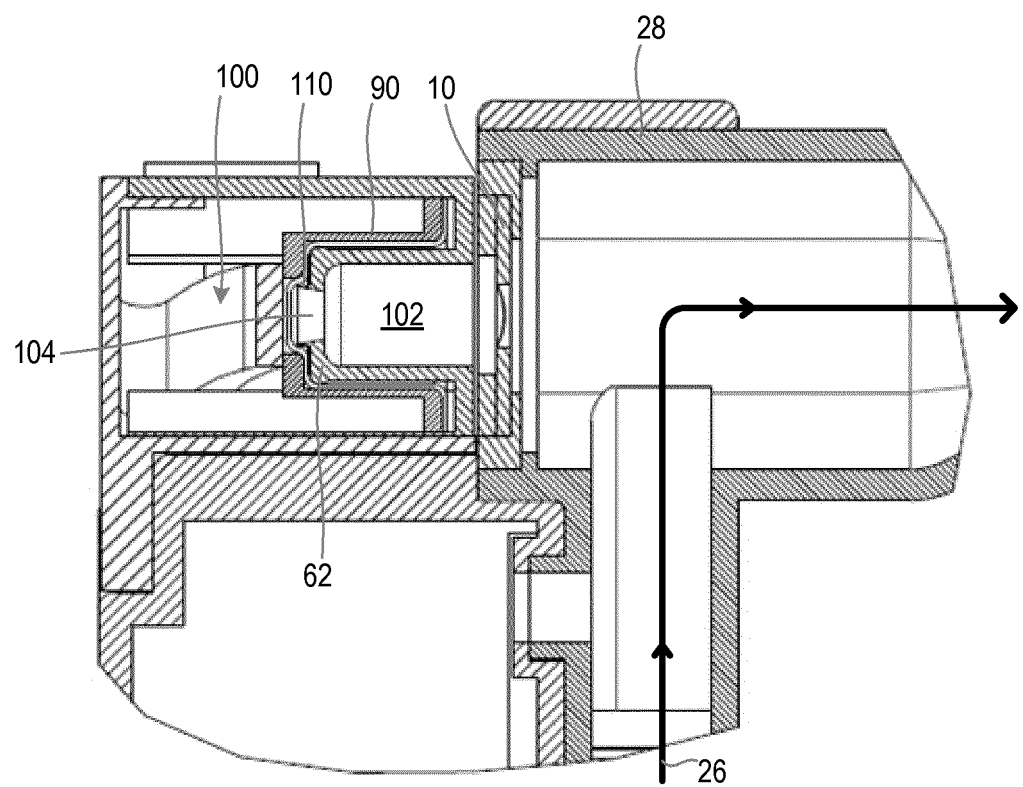
FIG. 17 is a part sectional view of a substance delivery module and control module.
Figure 18:
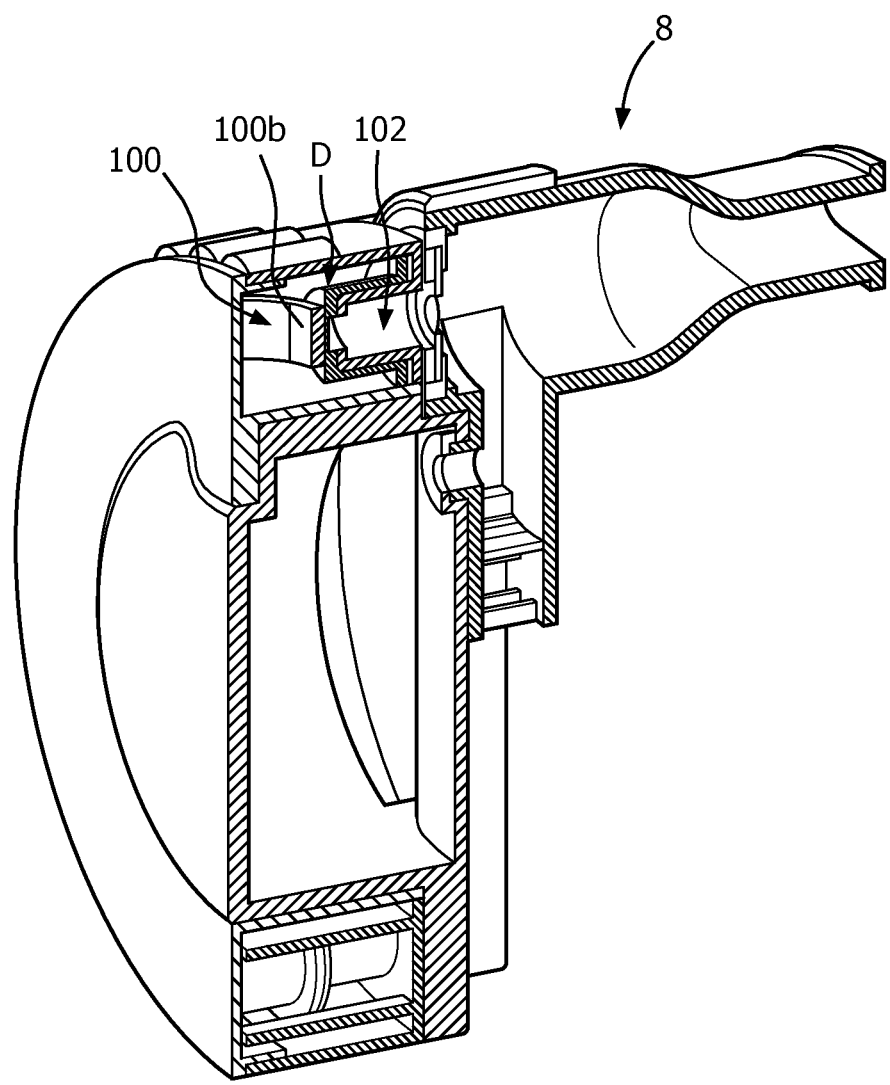
FIG. 18 is a sectional view of the nebulizer of FIG. 1.
Figure 19:
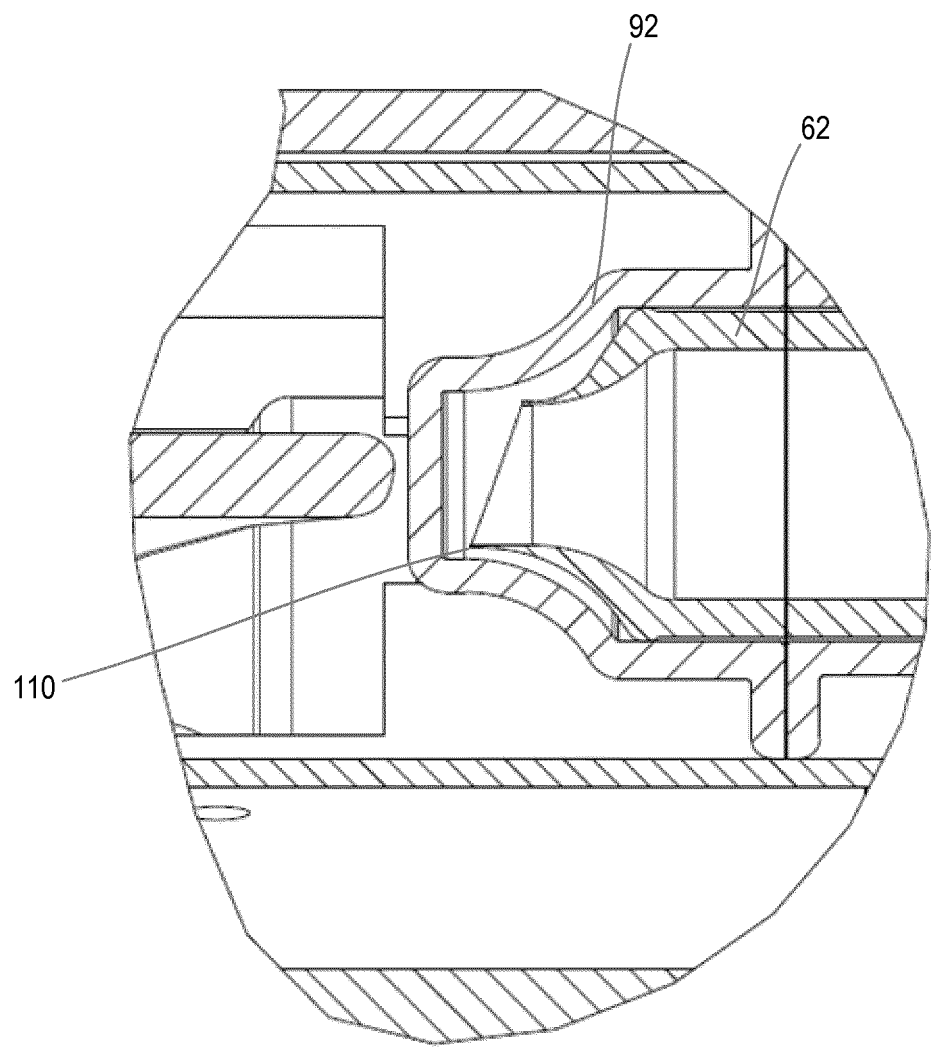
FIG. 19 is an enlarged view of a part of FIG. 18.
Figure 20:
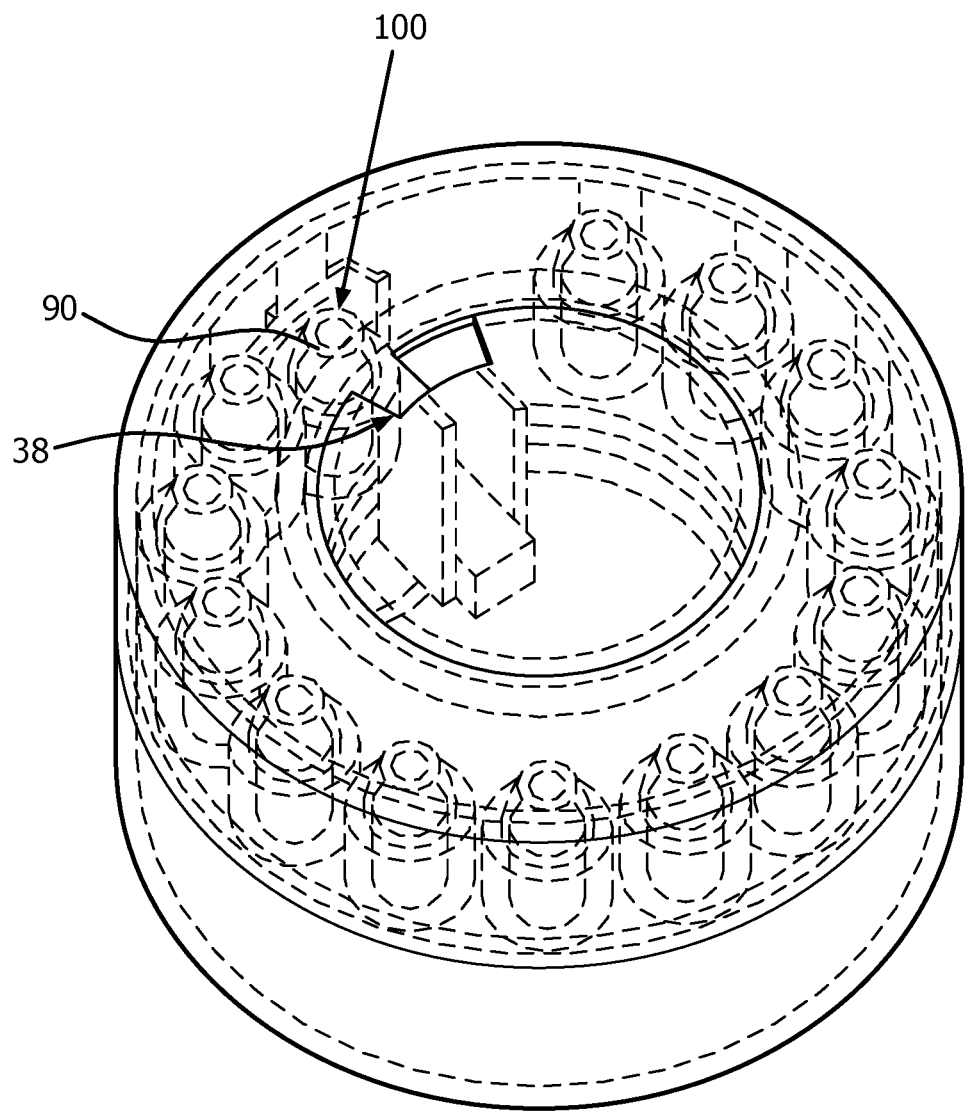
FIG. 20 is a perspective, partially transparent view of a substance delivery module mounted on a control module.
Figure 21:
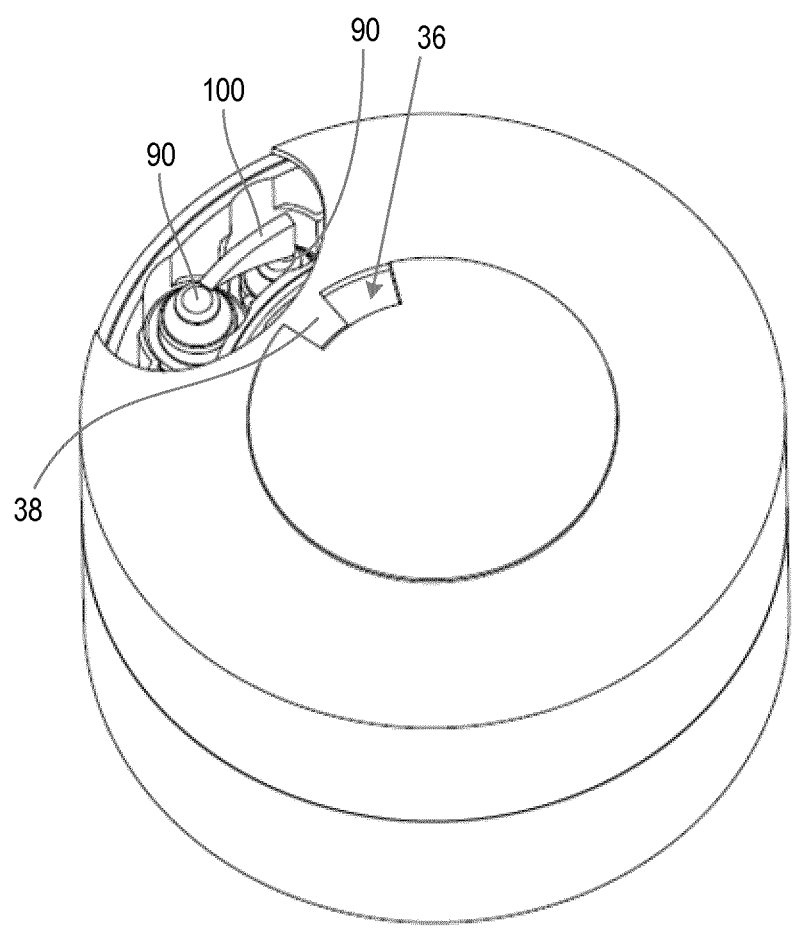
FIG. 21 is a perspective view of the modules of FIG. 20 showing a cut out view.

The cam 100, vial 90 and piston 62 can be seen in FIGS. 17 to 19 with the vial 90 fully displaced onto the piston 62. The cam 100 can be seen in FIGS. 17 and 18 to comprise an initial high rate section followed by a lower rate section in the form of a sprung arm 100b. The high rate section provides a high initial force which urges the vial 90 onto the first cutting element 110 of the piston 62, causing the first cutting element 110 to pierce the membrane 94 and allowing liquid from the vial 90 to start to enter the delivery passage 102 of the piston 62. The delivery passage 102 may have an internal diameter shaped to create a pressure gradient that encourages flow of the liquid in the vial into the passage 102. The internal surface of the piston may also be shaped to take advantage of gravitational or surface tension effects in encouraging liquid transfer. This is illustrated for example in the region D in FIG. 18. After the initial pressure that causes piercing of the membrane 94, the continuing rotation of the cartridge lid engages the sprung arm of the cam 100 over the vial 90, so forcing the vial 90 further onto the piston 62, guided by the sleeve 118. As the vial 90 advances, the second cutting element 116 engages the membrane and completely separates the membrane 94 from the cup 92, allowing the membrane 94 to remain on the leading face of the piston 62 as the piston progressively occupies the internal volume of the cup 92. By separating the membrane 94 from the cup 92 in this manner, the membrane is prevented from interfering with the seal between an outer diameter of the piston and inner diameter of the cup 92, so minimising leakage between the piston 62 and vial 90.

Continuing rotation of the lid 54 brings the sprung arm of the cam fully over the vial 90, as shown in FIGS. 17 to 22, until the guide lip 38 is returned to the left most edge of the guide recess 36. In this position, the vial 90 is fully forced onto the delivery piston 62, as shown in FIG. 19. The external surface of the piston is shaped substantially to displace the entire internal volume of the vial 90, so ensuring that a maximum amount of liquid is emptied from the vial and delivered to the through passage of the piston 62. The through passage 102 delivers the liquid from the vial 90 to the delivery passage 46 and so to the aerosol generator 10. The aerosol generator aerosolises the liquid and delivers the liquid in aerosol form into the inhalation flow path 26 to be entrained with inhaled air and drawn into the lungs of the patient. The cam 100, piston 62 and vial 90 thus cooperate to form a substance feed system that delivers a maximum amount of a dose of liquid substance to the aerosol generator 10.

A vent (not shown) may be mounted on the cartridge 52 adjacent each piston 62 and between the piston 62 and aerosol generator 10, to allow for escape of any air in the feed system during dispensing of the liquid substance. The vent may prevent liquid escape and may include a non return valve to prevent air entering the feed system between treatments. The vent may also allow air to replace liquid during aerosolization.

After dispensing the contents of the first vial 90 in the above described manner, the nebulizer 2 may be powered off until the next dose is due. At this point the patient powers on the device and repeats the above described steps, indexing the cartridge 52 to the next position and so placing the next piston and charged vial in the delivery position in front of the aerosol generator 10. The cartridge lid 54 only is then returned in the anti clockwise direction to its original position with respect to the control module 6, so engaging the cam 100 over the vial 90 to be dosed, forcing the vial 90 onto its delivery piston 62 and dispensing the contents of the vial via the piston 62 to the aerosol generator 10 and into the inhalation flow path 26. These processes may be repeated until all of the charged vials 90 in the substance delivery module 4 have been dispensed.

In other embodiments (not shown), the substance delivery module and nebulizer may be structured to support relative linear motion between the cam and vials. Thus a substantially linear cartridge and lid may support relative linear motion, such that for example the cartridge enters progressively into the lid to engage a cam located at an entrance to the cartridge lid. The cartridge and lid are sized such that the cartridge is fully received into the lid once all vials in the cartridge have been dispensed. In another alternative embodiment, the cartridge lid may be sized such that only a small portion of the cartridge located adjacent the mouthpiece is covered by the lid. The cartridge may progress from a first side of the lid to a second, opposite side of the lid as the vials in the cartridge are dispensed. The mechanism of indexing the cartridge and dispensing a vial through relative motion between the cartridge lid and the vial may operate substantially as described above with reference to the attached Figures.

Various control mechanisms within the nebulizer 2 may be used to manage the process of dispensing the substance from a vial 90 into the inhalation flow path 26 in aerosol form. For example, the flow control valve 20 may limit the flow rate at which air may be inhaled into the nebulizer, allowing patients to inhale for a longer time during each breath and so potentially reducing treatment time. The flow control valve may also prevent exhalation into the device 2. In addition, the dimensions and spring qualities of the cam 100 including the cam sprung arm 100b may be chosen to limit the speed with which the vial 90 is forced onto the delivery piston 62 and so to limit the transfer rate of the drug from vial to delivery piston and on to the aerosol generator.

The guide lip 38 and guide recess 36 also provide a form of control as well as guiding the patient in the assembly of the nebulizer 2. By limiting the relative clockwise rotation of the cartridge lid and cartridge with respect to the control module 6, the lip 38 and recess 36 ensure that the cartridge 52 can only ever be indexed by one position, ensuring a dose is not skipped. In addition, the cartridge cannot be indexed to the next position until the vial in the dispending position has been dispensed. This is because further clockwise rotation of the cartridge lid 54 and cartridge 52 can only be allowed by the guide lip 38 and guide recess 36 once the cartridge lid 54 has performed its anti clockwise rotation to return to its initial position, so bringing the cam 100 into engagement with the vial 90 in the dispensing position and dispensing the substance contained in the vial 90. A patient can verify that complete dispensing of the vial has been achieved by confirming that the guide lip 38 is fully engaged against the left side of the guide recess 36.

Another form of control may be provided by the RFID tag discussed above. Electronic tagging of the control module and substance delivery module may ensure that only certain substance delivery modules may be used with certain control modules. Thus if a control module 6 is to be restricted to use with only specific substances/substance delivery modules, the control module can be programmed such that functioning of the module and release of the solenoid lock 120 will only be permitted when the correct electronic tag recognition is registered. Electronic tagging of this nature may also enable tracking of how many and which substance delivery modules have been used with a particular control module 6. Additionally, the power supplied to the aerosol generator 10 may be tailored according to particular substance delivery modules charged with different substances. In this manner, the process of aerosolising the substance may be tailored to the particular substance contained in the substance delivery module. Similar tagging may be used with the mouthpiece 8 to control use of the mouthpiece 8 and feedback instructions to the patient. Such tagging may have benefits in facilitating patient monitoring, reminders for cleaning of the mouthpiece, replacement of the control module and/or mouthpiece when they have reached their recommended lifespan and/or reminders to restock with charged substance delivery modules 4. A mechanical key system may also be used to ensure certain control modules 6 may only be used with specific substance delivery modules 4.

The pressure sensor which is mounted in the control module 6 to protrude into the inhalation flow path may measure the timing of patient inhalation and compare this with the timing of drug dispensing via the device. In this manner, the device may indicate to a patient whether or not the timing of their inhalation is correctly matched with drug dispensing. The pressure sensor may be provided with a gel coating, allowing substances in contact with the inhalation flow path to be disinfected using alcohol or other solutions.

The aerosol generator may also communicate with the control module 6 to feedback a state of the feed system. For example, the aerosol generator 10 may detect a change in drive characteristics, for example by detecting a change in the impedance of the peizo mesh, indicating that all of the substance in the current vial has been dispensed and the feed system is now dry. This information may be fed back to the patient via a light, buzzer or other indicator, providing further confirmation of complete dispensing of a dose of substance. Similarly, if the feed system is detected to be dry immediately on indexing to a new position, the control module may indicate this to the patient. In the event of an incomplete dosing, for example if a patient pauses during dispensing of the drug, a visual reminder can be provided to the patient to complete the dispensing and then clean the mouthpiece 8 before recommencing by indexing to the next vial 90.

Further feedback may be provided via the control module 6 or the substance delivery module 4 to indicate the number of sealed vials remaining in the substance delivery module 4. This feedback may be provided by the cartridge and cartridge lid, linked to the indexing system, or may be provided via the control module using a counter.

The material of the mouthpiece 8, pistons 62 and aerosol generator 10 may comprise or be coated with an antimicrobial material (for example silver) or be treated with an antimicrobial process (for example ultra violet light) to reduce the formation of bacteria at sites of residual substance, saliva, condensate etc.

Embodiments of the present invention thus provide a substance delivery module and apparatus for delivery of a substance that are efficient and easy to use. The substance delivery module provides controlled dosing, with individual vials of substance each containing a single dose. Complete delivery of the dose is assured through the arrangement of the components forming the feed system. The feed flow path from vial through piston to aerosol generator is comparatively short, reducing to a minimum the surfaces that are wetted by the substance in passing, and so reducing substance wastage. In addition, by forcing the vial completely onto the piston, and dimensioning the piston to displace substantially the entire internal volume of the vial, maximum transfer of substance from the vial is assured. The delivery passage of the piston may be dimensioned to create a pressure gradient that further assists transfer of the substance from vial to piston and on to the aerosol generator. Embodiments of the invention thus reduce substance wastage and provide accurate substance dosing.

The shortened feed flow path also has advantages in the ease of use of the substance delivery module and apparatus. By reducing the surfaces wetted by the substance during delivery, the surfaces requiring regular cleaning are also reduced to a minimum. These surfaces are essentially found in the mouthpiece 8, meaning those surfaces requiring cleaning are found in a single component which may be removed and cleaned as required.

The dedicated delivery pistons help to ensure a greatly reduced risk of contamination. Each vial has a corresponding delivery piston that essentially forms the feed flow path for that vial, delivering the substance to the aerosol generator. Each new vial thus benefits from an unused feed flow path, meaning that different substances can be loaded in different vials and dispensed through the same apparatus. For example, a treatment course comprising different medicaments for morning and afternoon dispensing may be contained in a single substance delivery module, with the substance vials loaded in alternating pattern in the cartridge. Risk of contamination between the substances is minimised by the design of the delivery module and apparatus. A cleaning substance, for example a volatile cleaning solution such as ethanol may be included in one or more of the vials spaced around the apparatus. This may represent a cleaning position, dispensing of the vial by a patient allowing for cleaning of the substance flow path. The apparatus may be locked during this time to prevent a patient inhaling the cleaning substance.

Separating the wetted and contaminated surfaces between the three units of the apparatus also assists in maximising the usage life of the individual units. The substance delivery module may be rendered entirely disposable, a new module provided with each new course of treatment. The mouthpiece may be cleaned between uses and between treatment courses and may thus have a longer usage life for example of between one and 24 months. The control module which has minimal contact with the inhalation flow and feed paths may benefit from a longer usage life of several years, and with appropriate cleaning may be used by several different patients.

Patient involvement with the substance to be dispensed is also minimised. The substance delivery module can be provided to a patient ready loaded with sealed vials and for example completely sterilized after assembly and before delivery to the patient. The patient is merely required to load the substance delivery module onto the control module and dispense the substance as described above.

Embodiments of the invention also render the dispensing process easy for a patient to achieve. The patient is merely required to index the substance delivery module to load a new piston/vial combination into the dispensing position. A return spring may then be used to effect the return motion that engages the cam over the vial and dispensed the substance. Alternatively the patient may effect the return motion as required. The entire loading and dispensing process is achieved through simple rotational motion, with no requirement for a plunging motion or other action by the patient to dispense the substance.

It should be noted that the above-mentioned embodiments illustrate rather than limit the invention, and alternative embodiments may be envisaged without departing from the scope of the appended claims. The word "comprising" does not exclude the presence of elements or steps other than those listed in a claim, and the indefinite article "a" or "an" does not exclude a plurality. A single processor or other unit

The invention claimed is:

1. A substance delivery module comprising:
   an annular cartridge;
   a plurality of pistons and substance containers, wherein the substance containers are mounted within the annular cartridge, and wherein each one of the pistons is axially aligned with an associated one of the substance containers; and
   an actuator configured to sequentially engage each substance container and urge the substance container relative to the associated piston,
   wherein the actuator and the substance containers are mounted in the substance delivery module such that a motion of the actuator brings the actuator into axial alignment with the piston and substance container and subsequently forces the substance container onto the piston via rotation of the substance delivery module.

2. The substance delivery module as claimed in claim 1, wherein the piston is dimensioned to displace an internal volume of the substance container.

3. The substance delivery module as claimed in claim 1, wherein the piston comprises a passage extending therethrough.

4. The substance delivery module as claimed in claim 3, wherein the piston comprises a first cutting element, mounted on a leading surface of the piston.

5. The substance delivery module as claimed in claim 4, wherein the first cutting element is disposed about a leading opening of the piston passage.

6. The substance delivery module as claimed in claim 4, wherein the piston further comprises a second cutting element mounted about a rim of the leading surface of the piston.

7. The substance delivery module as claimed in claim 1, wherein the actuator and substance containers are mounted in the substance delivery module for relative rotational motion.

8. The substance delivery module as claimed in claim 1, further comprising an annular cartridge lid, and wherein the actuator is mounted on the annular cartridge lid.

9. The substance delivery module as claimed in claim 8, wherein the annular cartridge and the annular cartridge lid are adapted for relative rotational motion about an annular axis of the annular cartridge lid.

10. The substance delivery module as claimed in claim 8, wherein the actuator is mounted on an inner surface of the annular cartridge lid.

11. The substance delivery module as claimed in claim 9, further comprising a coupling element, releasably coupling the annular cartridge and the annular cartridge lid for motion.

12. The substance delivery module as claimed in claim 11, wherein the coupling element couples the annular cartridge and the annular cartridge lid for motion in a first direction and decouples the annular cartridge and the annular cartridge lid for motion in a second direction, opposite to the first direction.

13. An apparatus for delivering a substance in aerosol form, comprising:
   an aerosol generator;
   an aerosol delivery conduit in fluid communication with the aerosol generator; and
   a substance delivery module comprising:
      an annular cartridge;
      a plurality of pistons and substance containers, wherein the substance containers are mounted within the annular cartridge, and wherein each one of the pistons is axially aligned with an associated one of the substance containers;
      an actuator configured to sequentially engage each substance container and urge the substance container relative to the associated piston,
      wherein the actuator and the substance containers are mounted in the substance delivery module such that a motion of the actuator brings the actuator into axial alignment with the piston and substance container and subsequently forces the substance container onto the piston via rotation of the substance delivery module.

14. The apparatus as claimed in claim 13, further comprising a control module wherein the substance delivery module is mounted for rotation about at least part of the control module.

15. The apparatus as claimed in claim 14, further comprising a biasing element, mounted between a cartridge lid and one of the aerosol delivery conduit and the control module, and operable to urge the cartridge lid in a decoupling direction.

16. The apparatus as claimed in claim 14, further comprising a releasable locking element operable to fix a position of the annular cartridge relative to the control module.

17. The apparatus as claimed in claim 13, wherein at least part of the apparatus comprises an anti-microbial surface.

18. A method for delivering a substance in aerosol form, the method comprising:
   moving a substance delivery module in a first direction, the substance delivery module including an annular cartridge and a plurality of pistons and substance containers, wherein the substance containers are mounted within the annular cartridge, wherein each one of the pistons is axially aligned with an associated one of the substance containers, and wherein a motion in the first direction causes a leading opening of the piston to be in communication with an aerosol generator; and
   moving an actuator relative to the piston and substance container in a second direction, opposite to the first direction, a motion in the second direction causing the actuator to be axially aligned with the piston and the substance container, and subsequently forcing the substance container onto the piston via rotation of the substance delivery module.

* * * * *